United States Patent [19]

Chavkin

[11] Patent Number: 4,548,808
[45] Date of Patent: Oct. 22, 1985

[54] LONG-ACTING ANHYDROUS ANTIPERSPIRANT COMPOSITIONS CONTAINING TRIACETIN

[76] Inventor: Leonard Chavkin, 340 W. Dudley Ave., Westfield, N.J. 07090

[21] Appl. No.: 621,378

[22] Filed: Jun. 18, 1974

[51] Int. Cl.⁴ .................. A61K 7/32; A61K 7/34; A61K 7/38; A61K 9/12
[52] U.S. Cl. .................. 424/47; 424/DIG. 5; 424/65; 424/66; 424/67; 424/68; 424/69
[58] Field of Search .................. 424/65, 68, DIG. 5, 424/66, 67, 69, 47

[56] References Cited

FOREIGN PATENT DOCUMENTS

| 1121729 | 4/1982 | Canada | 424/68 |
| 2267086 | 11/1975 | France | 424/68 |
| 4969812 | 7/1974 | Japan | 424/68 |
| 197607 | 12/1974 | Japan | 424/365 |
| 0004355 | 1/1980 | Japan | 424/69 |
| 0112315 | 7/1982 | Japan | 424/69 |

OTHER PUBLICATIONS

Benton, American Perfumer & Cosmetics, 10/1963, vol. 78, No. 10, pp. 37-40.
Merck Index, 1976, 9th Edition, p. 1232.

Primary Examiner—Dale R. Ore
Attorney, Agent, or Firm—Omri M. Behr

[57] ABSTRACT

A substantially anhydrous antiperspirant composition having long-active, i.e., greater than 24 hour, deodorant activity is formed from a mixture of a micronized powdered antisperspirant active agent and triacetin. The resulting compositions are then formulated with conventional excipients to provide typical roll-on, stick and aerosol products.

7 Claims, No Drawings

LONG-ACTING ANHYDROUS ANTIPERSPIRANT COMPOSITIONS CONTAINING TRIACETIN

BACKGROUND OF THE INVENTION

Anhydrous non-alcoholic antiperspirant products are presently the most popular form of deodorants since they are the best accepted by consumers. This acceptance is due primarily to three factors, i.e., they have a low irritation potential, great antiperspirant efficacy, and go on dry so that they are non-sticky. Typical anhydrous non-alcoholic antiperspirant products comprise a dispersion of an antiperspirant active agent in a base comprised essentially of volatile silicones. The most commonly used antiperspirant active agents are aluminum or aluminum/zirconium acid salts. The present antiperspirant market is divided about equally among roll-on, stick and aerosol-type formulations. The most rapidly growing form is the stick since it has the most acceptable properties for application to the underarm.

Although the presently-sold products are excellent and represent advances over aqueous or alcohol-based products, they suffer from one major deficiency—their efficacy as deodorants diminishes rapidly after about twelve hours after application. While efforts have been made to overcome this deficiency by the addition of antimicrobial agents to the product to prolong deodorant action, these efforts have failed to produce long-acting deodorant compositions.

SUMMARY OF THE INVENTION

It has been found that substantially anhydrous compositions with long-acting, i.e., 24 hour or longer, deodorant activity may be formulated from a mixture comprising a micronized powdered antiperspirant active agent and triacetin. Such compositions may then be compounded in a conventional manner to provide products in roll-on, stick or aerosol formulations. The thus-formulated products have long-lasting deodorant activity with no sacrifice in any of the other desirable properties of the product. Thus, the products are not sticky, irritation is low, and the antiperspirant efficacy is not diminished.

DESCRIPTION OF THE PREFERRED EMBODIMENTS

The substantially anhydrous antiperspirant compositions of the present invention comprise 5-50 parts by weight, suitably 5-25 parts by weight, of a micronized powdered antiperspirant active agent. Among the suitable antiperspirant active agents which may be mentioned are the aluminum and aluminum/zirconium acid salts such as aluminum chlorhydroxide or aluminum zirconium hydroxy chloride, zinc chloride, zinc sulfate, zinc phenolsulfonate, aluminum sulfate, aluminum chloride, aluminum phenolsulfonate and aluminum bromide. There is also provided triacetin, said triacetin comprising between about 10 to about 95, suitably between about 20 to about 75 parts by weight of the total composition. In the preferred embodiment of the invention, the substantially anhydrous antiperspirant compositions comprise about 25 parts by weight of the micronized powdered antiperspirant active agent suitably buffered with glycine, and about 75 parts by weight of triacetin.

The compositions of the present invention can be conventionally formulated into a wide variety of typical antiperspirant/deodorant products suitable for consumer use.

A roll-on type product can be prepared comprising the basic anhydrous antiperspirant composition in a suspension with clays such as Bentone (available from N.L. Industries), or fumed silicas such as Cab-O-Sil (available from Cabot Corp.). The suspension is then marketed in the well-known roll-on applicator. Optionally, fragrance and/or coloring agents can be added to enhance the market appeal of the product.

A stick type product can similarly be prepared by gelling the anhydrous antiperspirant composition with conventional gelling agents. Typical gelling agents are those such as fatty alcohols, particularly fatty alcohols such as behenyl alcohol, stearyl alcohol, cetyl, palmityl or myristyl alcohols. As in the case of roll-on type products, other excipients, such as fragrance and/or coloring agents can be added to the final formulation.

To prepare a conventional aerosol-type product, the anhydrous antiperspirant composition is first formulated in a suspension as for a roll-on-type product. The resulting suspension is then blended according to standard procedures in a blend of liquified hydrocarbon propellants. Typically, the suspension composition comprises about 5-35% of the formulation and the propellant blend comprises about 65-95% of the formulation. Such aerosol formulations may, of course, optionally contain fragrance and/or other additives to appeal to the consumer.

The methods of manufacture for the final consumer product containing anhydrous antiperspirant compositions of the present invention are all standard in the consumer product art. Likewise, the conventional excipients used in specific formulations are all well-known in the art.

The special advantage of the compositions of the present invention lies in the especially desirable long-acting deodorant activity of the composition when formulated with conventional excipients into typical consumer antiperspirant/deodorant products. For example, in clinical trials with normal adults, improved deodorancy has been noted for at least 24 hours after the last application. While the antiperspirant activity of conventional compositions can be measured for prolonged periods of time after the last application (up to 48 hours), the return of objectionable underarm odor can be perceived beginning about 12 hours post-application. Since common usage of antiperspirant/deodorant products involves bathing and reapplication of the product at 24 hour intervals, the compositions of the present invention fully and completely satisfy the requirements of the consumer, whereas conventionally formulated products begin to fail after 12 hours. This long-acting effect of the compositions of the present invention is especially surprising since very effective antimicrobial agents such as the antiperspirant active agents themselves or quaternary or phenolic antimicrobials lose their efficacy after 12 hours in the axilla in normal use.

The following Examples describe in detail compositions and formulations illustrative of the present invention. It will be apparent to those skilled in the art that many modifications, both of materials and methods, may be practiced without departing from the purpose and intent of this disclosure.

EXAMPLE I

Roll-On

| | |
|---|---|
| 25.00 parts | Aluminum Chlorohydrate Powder |
| 2.50 parts | Fumed Silica, (Cabosil M-5) Cabot Corp. |
| 72.50 parts | Triacetin |
| 100.00 parts | |

All parts are by wt.

Procedure:

To the Triacetin, add the Aluminum Chlorohydrate powder under high speed stirring. When uniformly dispersed, slowly add the fumed silica and mix till the batch is uniform.

EXAMPLE II

Roll-On

| | |
|---|---|
| 25.00 parts | Aluminum/Zirconium Tetrachlorohydrate Glycine Complex Powder |
| 3.00 parts | Fumed Silica, Cabosil M-5, Cabot Corp. |
| 0.20 parts | Fragrance |
| 71.80 parts | Triacetin |
| 100.00 parts | |

All parts are by wt.

Procedure:

Same as Example I.

EXAMPLE III

Roll-On

| | |
|---|---|
| 25.00 parts | Aluminum Chlorohydrate Powder |
| 22.00 parts | Triacetin |
| 20.00 parts | Alcohol, Ethyl Anhydrous |
| 0.20 parts | Fragrance |
| 29.80 parts | Volatile Silicone #03314, SWS Corp. D-4 Powder |
| 3.00 parts | Fumed Silica, Cabosil M-5, Cabot Corp. |
| 100.00 parts | |

All parts are by wt.

EXAMPLE IV

Stick

| | |
|---|---|
| 25.00 parts | Aluminum Chlorohydrate, Powder |
| 12.00 parts | Stearyl Alcohol |
| 0.30 parts | Fragrance |
| 62.70 parts | Triacetin |
| 100.00 parts | |

All parts are by wt.

Procedure:

Heat the Stearyl Alcohol and Triacetin to 150° F. Add the Aluminum Chlorohydrate powder to the batch under high speed stirring, add the fragrance and package in an appropriate container.

EXAMPLE V

Stick

| | |
|---|---|
| 25.00 parts | Aluminum/Zirconium Tetrachlorohydrate glycine complex powder. |
| 10.00 parts | Stearyl Alcohol |
| 2.00 parts | Castor Wax MP80, partially Hydrogenated Castor Oil (N.L. Inc.) |
| 0.30 parts | Fragrance |
| 62.70 parts | Triacetin |
| 100.00 parts | |

All parts are by wt.

Procedure:

Heat the Triacetin, Stearyl Alcohol and Castor Wax to 180° F., add the Aluminum/Zirconium/Glycine powder to the batch with high speed mixing. Cool batch to 140° F. Add the fragrance and package in appropriate container.

EXAMPLE VI

Aerosol

| | |
|---|---|
| 12.00 parts | Aluminum Chlorohydrate, ultra fine powder |
| 17.50 parts | Triacetin |
| 0.50 parts | Fumed Silica, Cabosil M-5, (Cabot Corp.) |
| 0.20 parts | Fragrance |
| 29.80 parts | Propellant 142, DiFluoro Mono Chloro Methane |
| 40.00 parts | n-Butane, Propellant A-17 |
| 100.00 parts | |

All parts are by wt.

Procedure:

To the Triacetine and perfume add the required amount of aluminum chlorohydrate powder with high speed mixing. Add the fumed silica to the batch and continue mixing. Pass the batch through a "Tri Homo" homogenizer to insure that there are no particle agglomerates. Add the required amount of this concentrate to a suitable aerosol can, crimp on a suitable valve and then pressurize the cans with the required amount of propellants.

I claim:

1. A substantially anhydrous antiperspirant composition having enhanced deodorant properties comprising
    (a) 5–50 parts by weight of a micronized powdered antiperspirant active agent and
    (b) 10–95 parts by weight of triacetin.

2. A composition of claim 1 wherein the antiperspirant active agent is aluminum chlorhydroxide.

3. A composition of claim 1 wherein the antisperspirant active agent is aluminum zirconium hydroxy chloride.

4. A composition according to claim 1 in admixture with conventional excipients to provide a roll-on type antiperspirant composition.

5. A composition according to claim 1 in admixture with conventional excipients to provide a stick-type antiperspirant composition.

6. A composition according to claim 1 in admixture with conventional excipients to provide an aerosol antiperspirent composition.

7. A composition according to claim 1 comprising 20–30 parts by weight of the antiperspirant active ingredient buffered with glycine, and 70–80 parts by weight of the triacetin.

* * * * *

UNITED STATES PATENT AND TRADEMARK OFFICE
CERTIFICATE OF CORRECTION

PATENT NO. : 4,548,808
DATED : October 22, 1985
INVENTOR(S) : Leonard Chavkin

It is certified that error appears in the above-identified patent and that said Letters Patent is hereby corrected as shown below:

On the title page, Item /22/ reading "Filed: Jun. 18, 1974" should read -- Filed: Jun. 18, 1984 --.

Signed and Sealed this

Twenty-seventh Day of May 1986

[SEAL]

Attest:

DONALD J. QUIGG

Attesting Officer

Commissioner of Patents and Trademarks